(12) United States Patent
Reina et al.

(10) Patent No.: US 11,678,851 B2
(45) Date of Patent: Jun. 20, 2023

(54) X-RAY IMAGE DETECTOR HOLDER AND MOUNTING DEVICE AND METHOD FOR COMMERCIAL X-RAY APPLICATIONS

(71) Applicants: Leo Reina, Cary, IL (US); Steven A. Gdula, Crystal Lake, IL (US); James Sorgani, Cary, IL (US)

(72) Inventors: Leo Reina, Cary, IL (US); Steven A. Gdula, Crystal Lake, IL (US); James Sorgani, Cary, IL (US)

(73) Assignee: X-Ray Cassette Repair Co., Inc., Crystal Lake, IL (US)

(*) Notice: Subject to any disclaimer, the term of this patent is extended or adjusted under 35 U.S.C. 154(b) by 0 days.

(21) Appl. No.: 17/494,566

(22) Filed: Oct. 5, 2021

(65) Prior Publication Data

US 2022/0133250 A1    May 5, 2022

Related U.S. Application Data

(63) Continuation of application No. 16/672,454, filed on Nov. 2, 2019, now Pat. No. 11,134,905.

(60) Provisional application No. 62/755,091, filed on Nov. 2, 2018.

(51) Int. Cl.
   *A61B 6/00*    (2006.01)

(52) U.S. Cl.
   CPC .......... *A61B 6/4291* (2013.01); *A61B 6/4411* (2013.01); *A61B 6/4283* (2013.01)

(58) Field of Classification Search
   CPC ....... A61B 6/4233; A61B 6/56; A61B 6/5205; A61B 90/39; A61B 2090/3966; A61B 6/4405
   See application file for complete search history.

(56) References Cited

U.S. PATENT DOCUMENTS

2013/0064351 A1* 3/2013 Urbon ............... A61B 6/56
                                                    378/189

* cited by examiner

*Primary Examiner* — Don K Wong
(74) *Attorney, Agent, or Firm* — Clifford H. Kraft

(57) ABSTRACT

A device for attaching an x-ray image detector holder to a commercial structure such as a pipe so that the modern digital image detector can be used in analysis and inspection. The x-ray image detector holder attach device is constructed to be attached to a structure and can include a flat image detector holder part, the image detector holder part having at least one peripheral slot; a structure contact part constructed to be strapped to a structure to be x-rayed, the structure contact part having a key sized to mate with the peripheral slot, the key having a lock constructed to hold the key in the peripheral slot; the structure contact part can be a means to attach it to the structure to be x-rayed such as a strap or suction cups.

4 Claims, 10 Drawing Sheets

Prior Art

US 11,678,851 B2

X-RAY IMAGE DETECTOR HOLDER AND MOUNTING DEVICE AND METHOD FOR COMMERCIAL X-RAY APPLICATIONS

This is a continuation of application Ser. No. 16/672,454 filed Nov. 2, 2019 which was related to and claimed priority from U.S. Provisional Patent application No. 62/755,091 filed Nov. 2, 2018. application Ser. No. 16/672,454 and 62/755,091 are hereby incorporated by reference in their entireties.

FIELD OF THE INVENTION

The present invention relates generally to commercial x-ray applications and more particularly to an x-ray image detector panel holder mounting device and method that allows a wide range of x-ray image detectors to be used in commercial applications.

DESCRIPTION OF THE PROBLEM SOLVED

X-ray has been used commercially to detect defects in commercial structures including pipelines, bridges and buildings. These applications are often conducted under demanding conditions not experienced in typical medical x-ray applications. X-ray image detectors are sensitive and, in the case of digital radiographic panels, expensive. Such commercial applications include an x-ray generator and an x-ray image detector panel that can be of various types, placed in a panel holder or encasement designed to provide rigidity and protection for the detector during the x-ray operation. The panel holder function is to hold the x-ray image detector on the surface of the object to allow a capture of the x-ray image. Devices that capture x-ray images range from photographic film to modern digital photosensitive devices. The detector holder holds the sensitive photo-device or surface flat and secure and allows handling.

However, x-ray image detectors are nevertheless very sensitive to shock, heat and rough handling. Unfortunately, shock, heat and rough handling is very common in commercial applications such as x-raying a pipe or building structure. In particular, the very expensive x-ray image detectors are usually destroyed and rendered useless if dropped, bent or exposed to excessive heat.

Prior art techniques for holding an x-ray image detector against an object usually consists of tying the detector in place with straps or the like. This has many disadvantages. First, the detector is a flat plate-like element, and the pipe or structure is cylindrical or has some other non-flat surface shape. This many times can cause the detector to not lie orthogonal to the x-ray beam, to shift position after being secured or to be bent by excessive strapping force. Second, such makeshift securing of the detector leads to detectors being subjected to damaging stresses, or to fall loose or other movement that destroys the detector. Moreover, when the panel is placed on a hot surface the sensitive electronics in the panel can be damaged or render imperfect images of the subject being x-rayed.

It would be tremendously advantageous to have a device and method to secure an x-ray image detector to a commercial structure such as a pipe so that it is easy to mount, remains orthogonal to the beam, is securely held in position, safe from shifting or becoming loose and falling, and is held in a position above the object to prevent damage from over heating

SUMMARY OF THE INVENTION

The present invention relates to a device for attaching an x-ray image detector holder to a commercial structure such as a pipe or other metal surface so that the digital detector can be safely and securely held in position for accurate analysis and inspection. The x-ray image detector holder device is constructed in such a manner to allow it to be attached to a structure and can include a flat detector holder part, the detector holder part having at least one peripheral slot, a structure contact part constructed to be strapped or magnetically attached to the structure to be x-rayed, the structure contact part having a key sized to mate with the peripheral slot in the detector holder, the key having a lock constructed to hold the key in the peripheral slot, the structure contact part having a means to attach it to the structure to be x-rayed such that the image detector, and detector encasement holder are positioned above the surface being x-rayed.

DESCRIPTION OF THE FIGURES

Attention is now directed to several drawings that illustrate features of the present invention.

Several figures and illustrations have been provided to aid in understanding the present invention. The scope of the present invention is not limited to what is shown in the figures.

DESCRIPTION OF THE PREFERRED EMBODIMENTS

The present invention relates to a device and method of securing an x-ray image detector panel holder to a pipe or other structure.

Figure 1A:
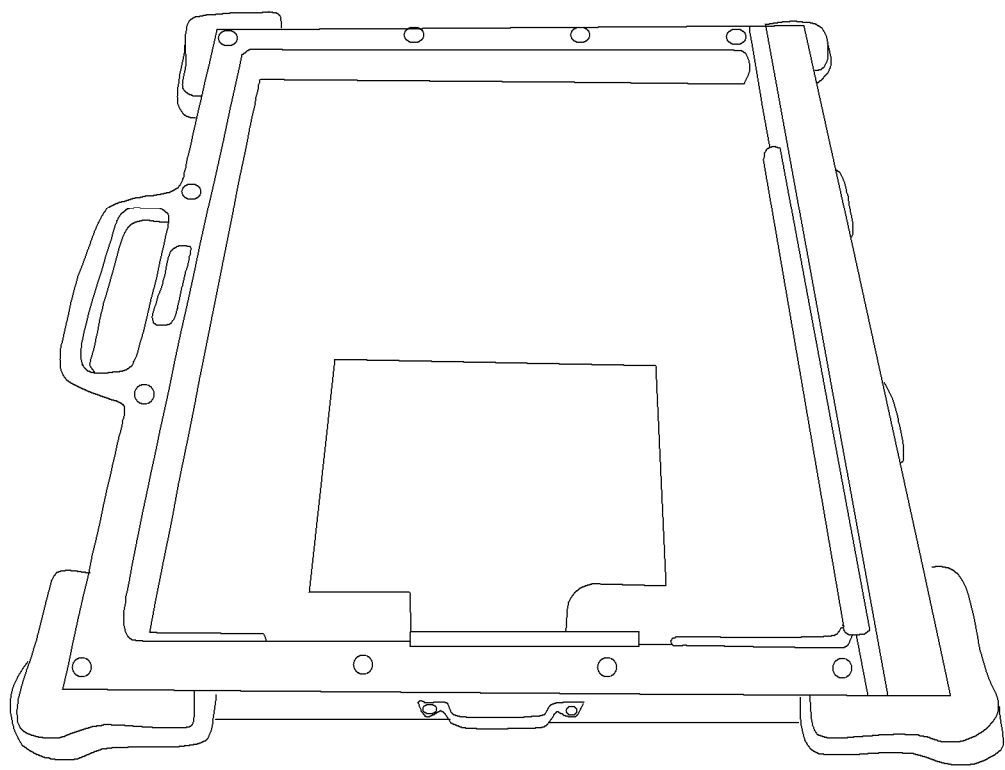
FIG. 1A is a prior art x-ray image detector holder.

FIG. 1A shows a prior art x-ray panel holder. It can clearly be seen to be a delicate plate-like device with glass or other fragile material covering the photosensitive surface. Straps or cords loop through or attach to the metal handles for securing the device.

Figure 1B:
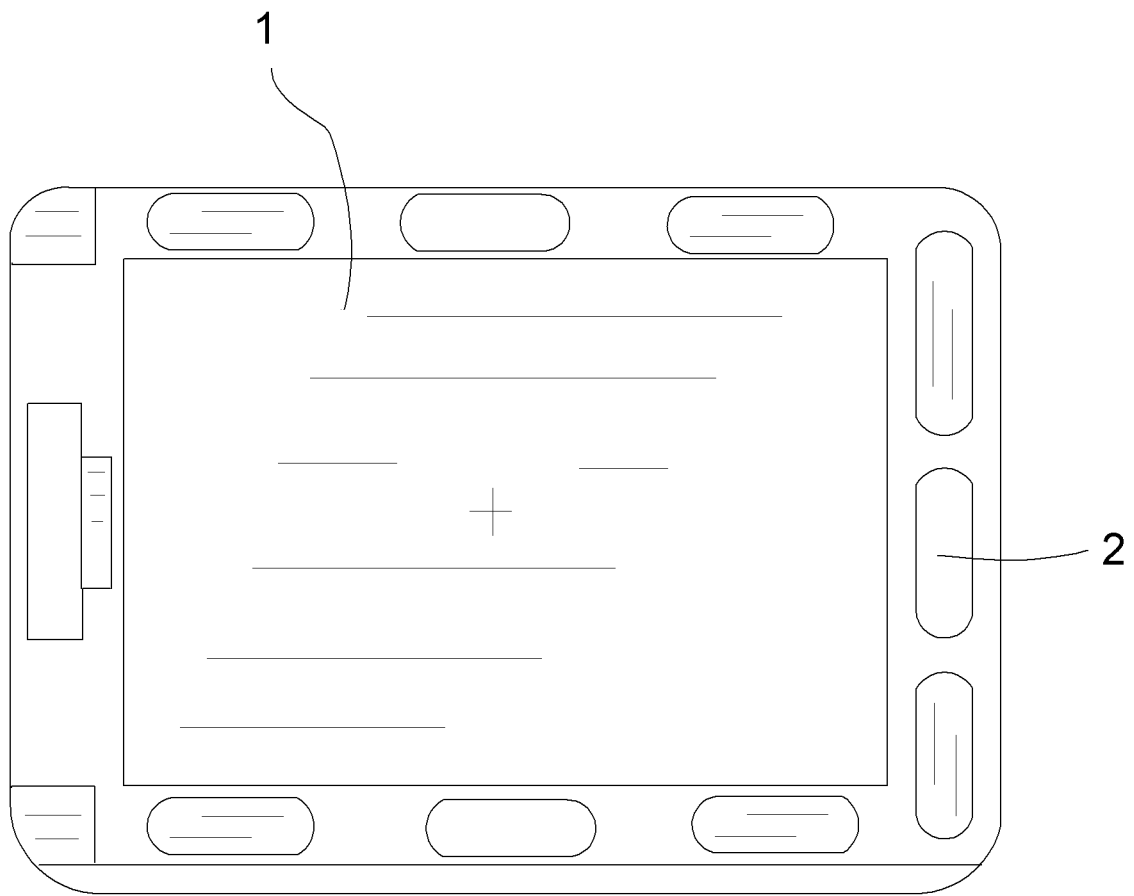
FIG. 1B is an embodiment of the x-ray image detector holder part of the present invention.

A particular embodiment of the present invention secures the x-ray image detector holder to a pipe; larger sized holders can be used to affix the detector holder to larger diameter pipes. Other embodiments can secure the detector holder to any shaped structure having either metallic and non-metallic surfaces. The particular embodiment includes three parts: a detector panel holder, a detector holder part to secure the detector holder and a pipe strap part. FIG. 1B shows an embodiment of the detector holder part of the present invention. The central part 1 holds the x-ray image detector, while the periphery includes handles with slots 2. The slots 2 are constructed and shaped to engage the pipe strap part.

Figure 2:
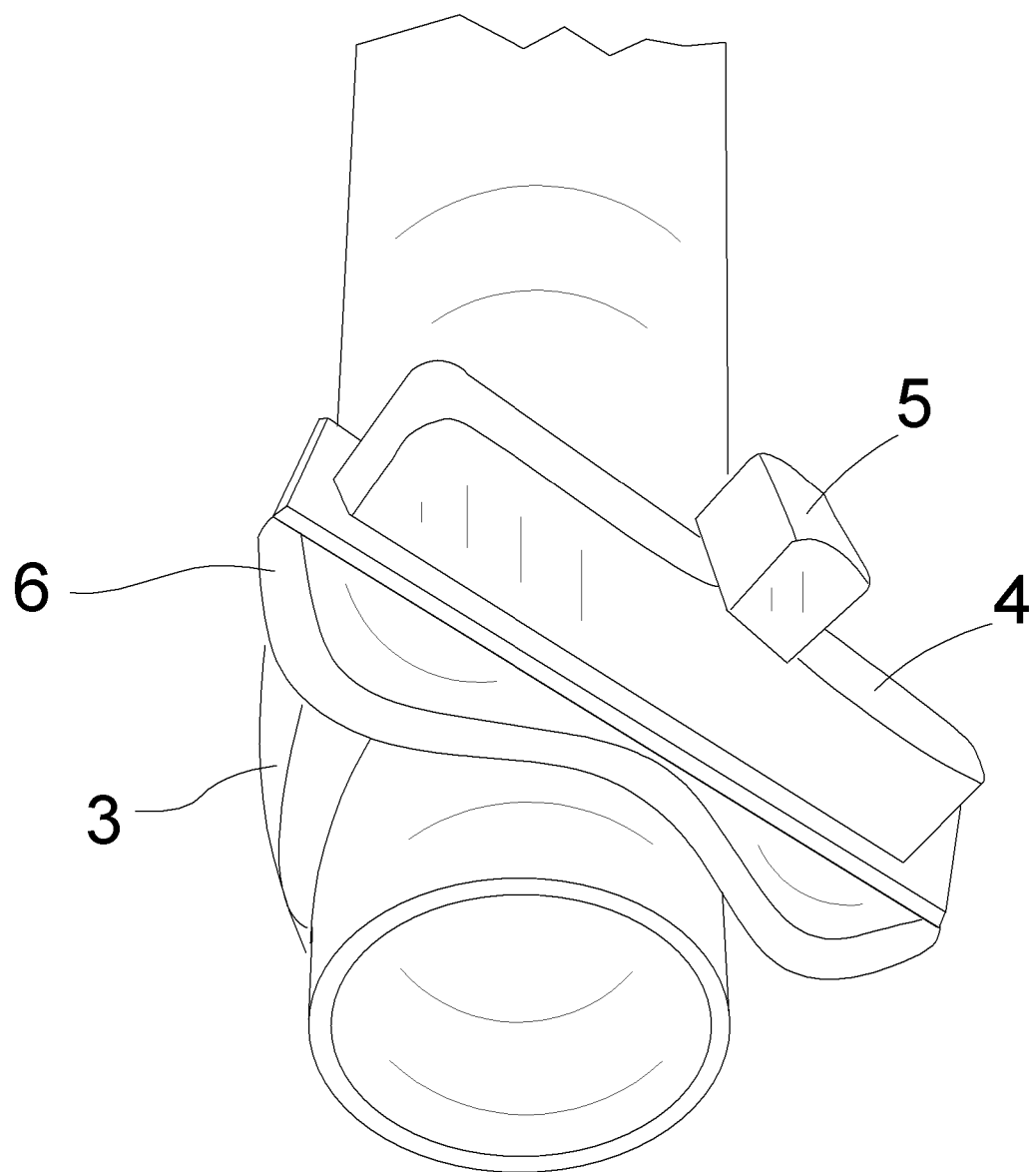
FIG. 2 is an embodiment of a pipe strap holder part of the present invention.

FIG. 2 shows an embodiment of the pipe strap part. A central section 6 is constructed to prevent the panel from contacting the surface of the pipe, which in some applications may be hot or cold. Contact of the panel holder with a hot surface can distort the image and/or damage the sensing devices in the x-ray cassette detector panel. This pipe strap part can be manufactured in different sizes to accommodate different ranges of pipe diameters. It can also be configured to affix to flat surfaces and held in place with magnets or suction cup. A key 4 matches the slot 2 in the detector holder part. A lock 5 secures the key 4 in the slot 2. A strap 3 secures the entire device to a pipe.

Figure 3:
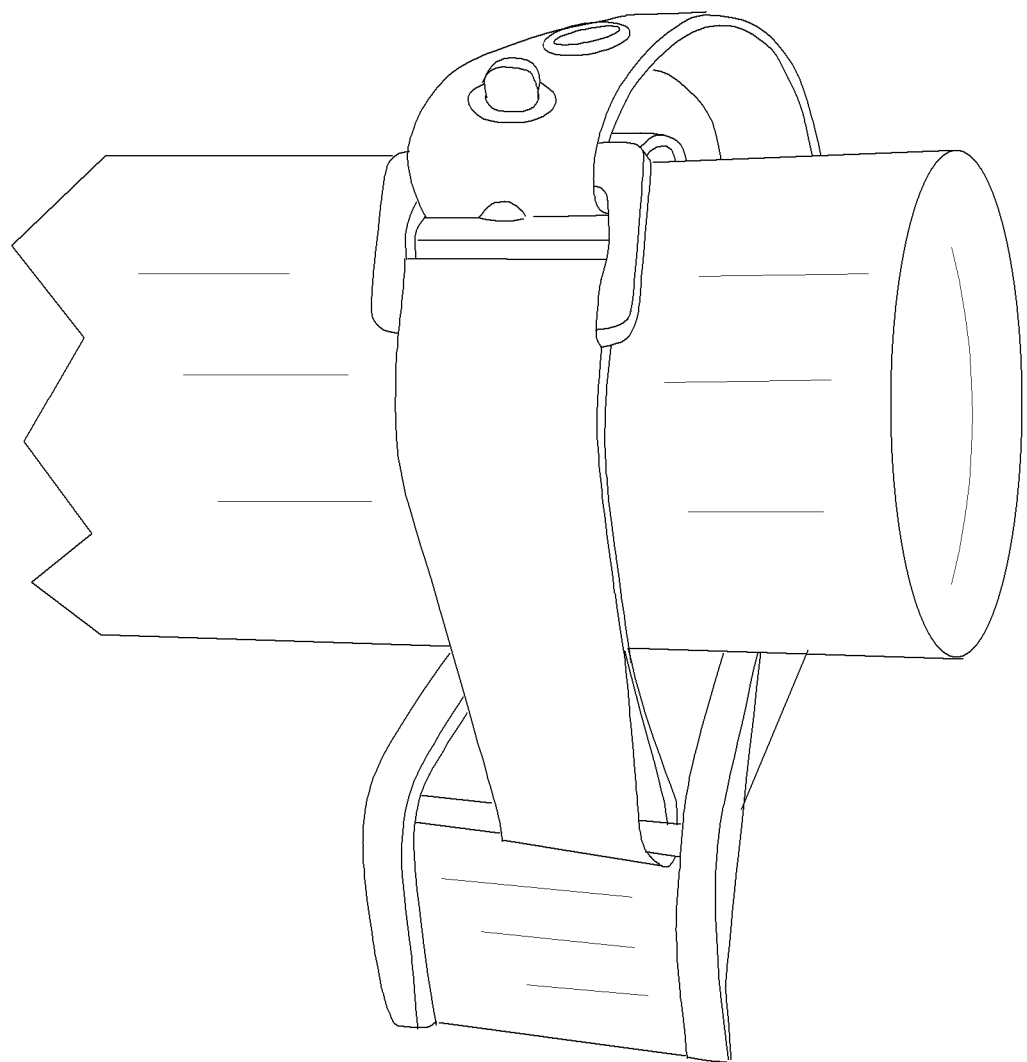
FIG. 3 shows the pipe strap part of FIG. 2 strapped to a pipe.
Figure 4:
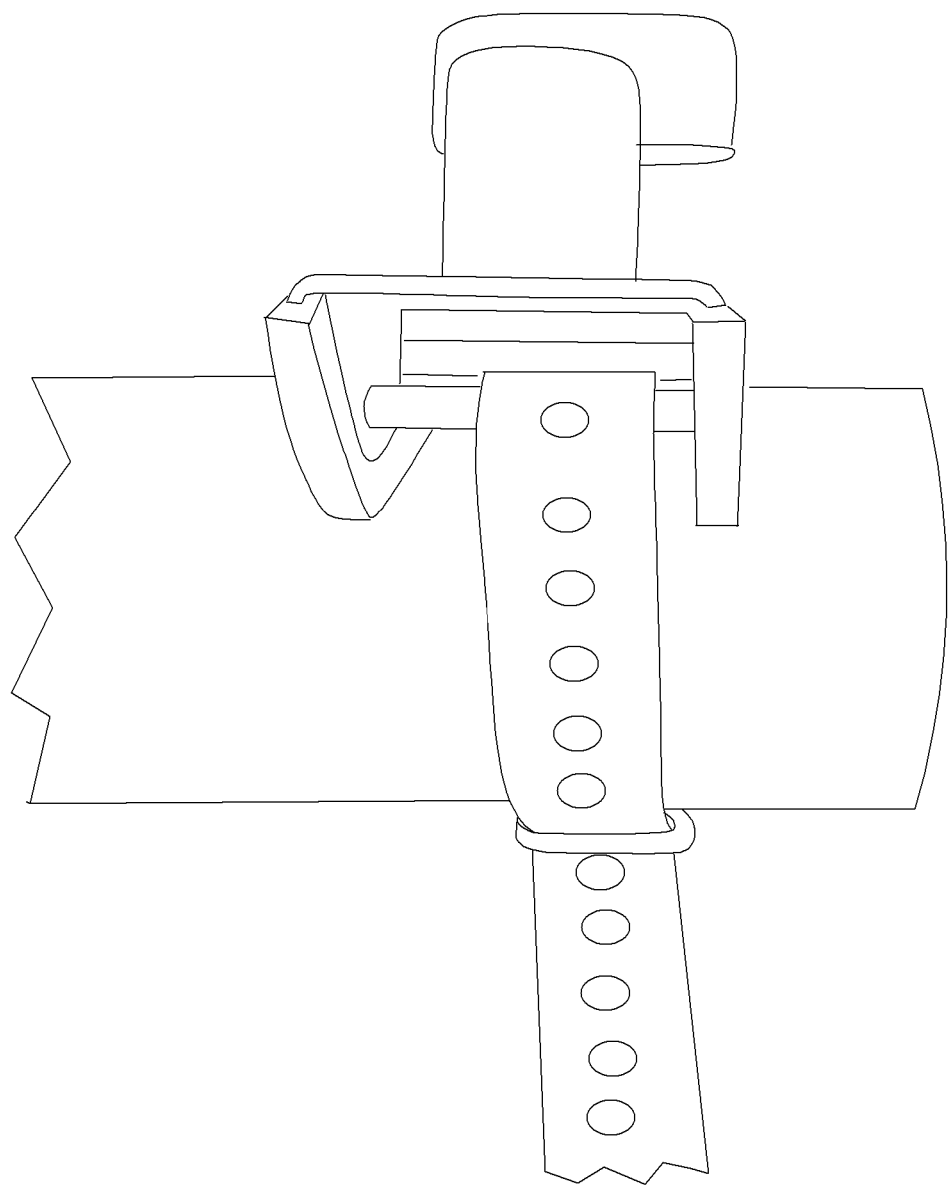
FIG. 4 is a different view of the part shown in FIG. 3.
Figure 5:
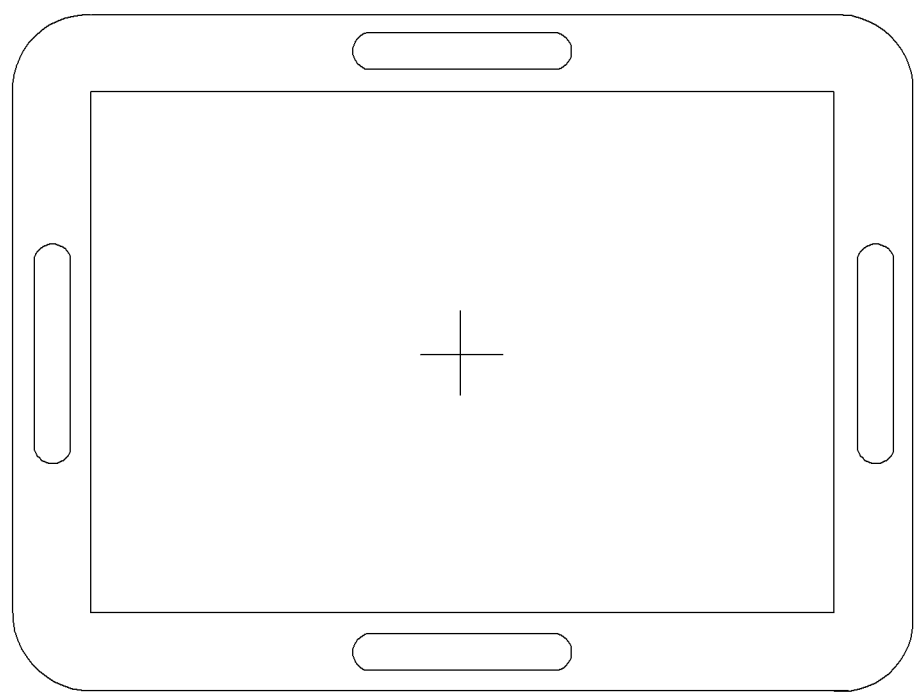
FIG. 5 is a different view of the detector holder part shown in FIG. 1B.

FIGS. 3-4 show different views of the pipe strap part secured to a pipe. FIG. 5 shows a different view of the detector holder part.

Figure 6:
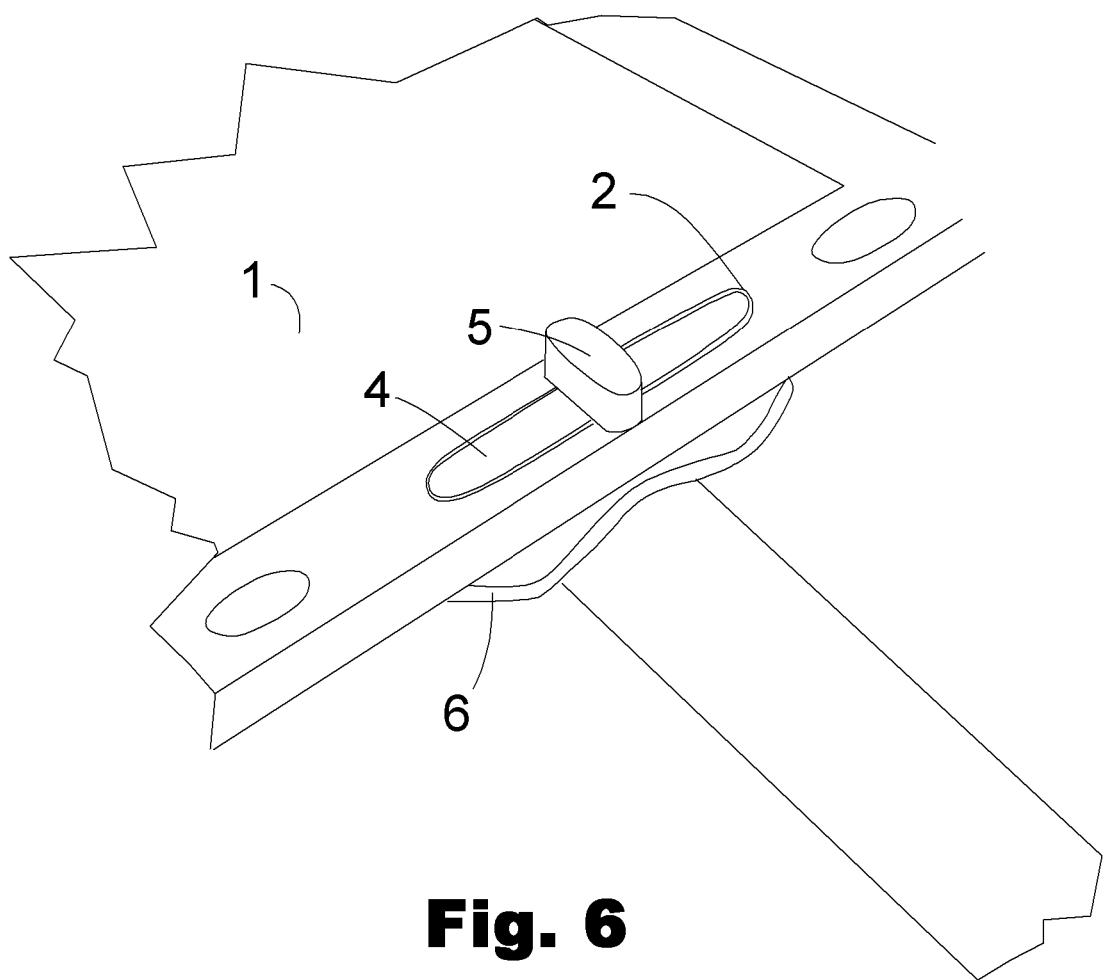
FIG. 6 shows the pipe strap part mated with the detector holder part.

FIG. 6 shows the entire device assembled and strapped to a pipe. The flat central part of the detector holder frame 1 holds the x-ray image detector. The protruding key 4 slips into the elongated slot 2 and is secured by the somewhat elongated lock 5. The strap 3 holds the device in position on the pipe. The lock 5 can be turned to lock and hold the device to the x-ray image detector holder frame 1 by providing a bias that pulls the protruding key 4 against the detector holder frame 1.

The device and parts of the present invention can be made from any rigid material with firm plastic being preferred. The strap can be a fiber strap that includes a buckle, VELCRO® or other attachment device.

The detector holder part can attach in a similar way to other older parts designed for other types of structures besides pipes. In particular, a flat strap part can fit a beam or other flat or rectangular structure.

Figure 7:
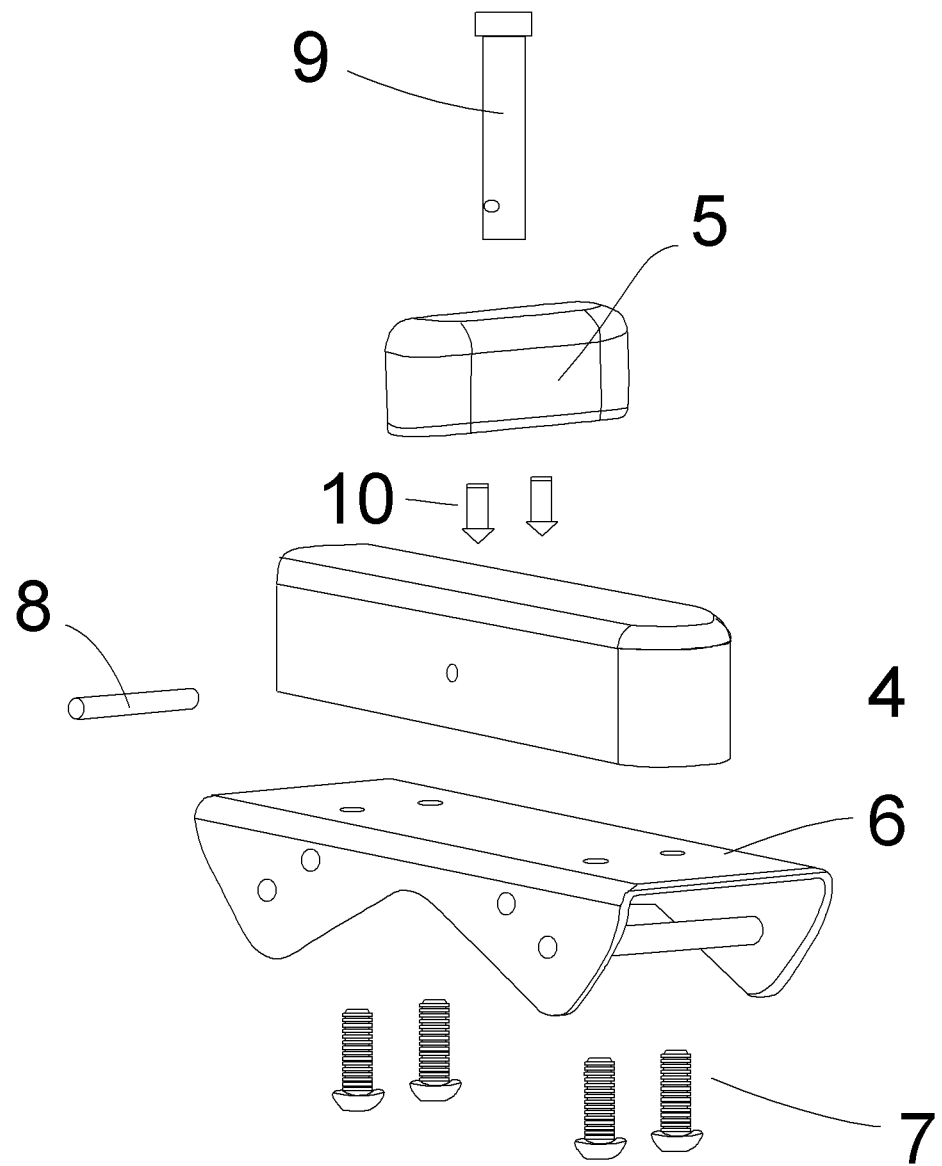
FIG. 7 shows an exploded view of the parts making up an embodiment of the present invention

FIG. 7 shows an exploded view of the parts making up an embodiment of the present invention. A bracket 6 attached to a key 4. Two pins 10 hold the lock 5 to the key 4. An insertion pin 8 can also be used. A center axle 9 extends through the lock 5 into the key 4 and allows the lock 5 to turn. Four bolts 7 attach the key 4 to the bracket 6.

Figure 8:
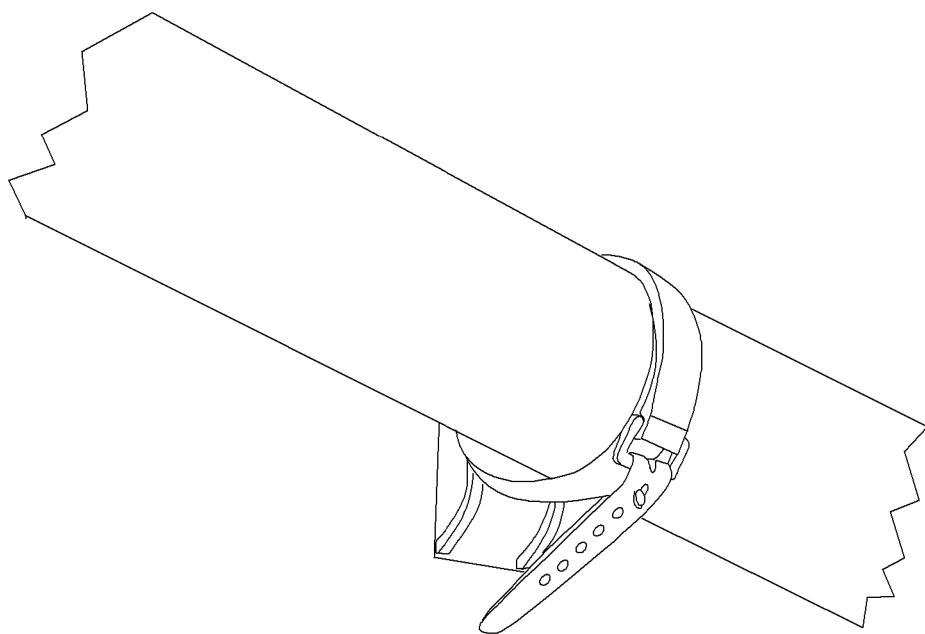
FIG. 8 shows a different view of a pipe strapped to a pipe.

FIG. 8 shows another view of the device strapped to a pipe.

Figure 9:
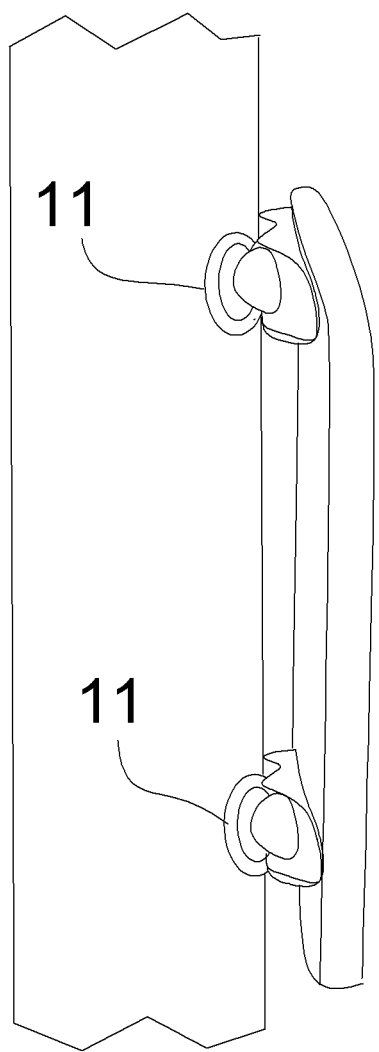
FIG. 9 shows an embodiment of the present invention using suction cups.

FIG. 9 shows an alternate embodiment of the device that uses suction cups 11 rather than a strap to attach to the pipe or other object.

Several descriptions and illustrations have been presented to aid in understanding the present invention. One with skill in the art will realize that numerous changes and variations may be made without departing from the spirit of the invention. Each of these changes and variations is within the scope of the present invention.

We claim:

1. An x-ray image detector holder constructed to secure an x-ray image detector to a structure comprising:
    a flat image detector holder part, the image detector holder part having at least one peripheral slot;
    a structure contact part constructed to be attached to a structure to be x-rayed, the structure contact part having a key sized to mate with the peripheral slot, the key having a rotating lock constructed to hold the key in the peripheral slot;
    the structure contact part having at least two suction cups to attach it to the structure to be x-rayed.

2. The x-ray image detector holder of claim 1 wherein the structure contact part is constructed to attach to a pipe.

3. The x-ray image detector holder of claim 1 further including a plurality of suction cups.

4. The x-ray image detector holder of claim 1 wherein the structure to be x-rayed is a pipe.

\* \* \* \* \*